United States Patent [19]

Schwartz et al.

[11] 4,255,788
[45] Mar. 10, 1981

[54] PHASING DETECTOR FOR CONTINUOUS FLOW SYSTEMS

[75] Inventors: P. Christopher Schwartz, Beltsville; Richard I. Spielberg, Rockville, both of Md.

[73] Assignee: American National Red Cross, Washington, D.C.

[21] Appl. No.: 16,532

[22] Filed: Mar. 1, 1979

[51] Int. Cl.³ .............................. 356 39; G01N 33/48
[52] U.S. Cl. .................................. 364/416; 364/510; 364/526
[58] Field of Search .............. 364/416, 509, 510, 497, 364/499, 526; 128/2 F, 2 G; 356/39–43

[56] References Cited

U.S. PATENT DOCUMENTS

| | | | |
|---|---|---|---|
| 3,704,097 | 11/1972 | Capuano | 364/509 X |
| 3,728,080 | 4/1973 | Moran | 364/499 X |
| 3,777,127 | 12/1973 | Goetchius et al. | 364/497 |
| 3,832,135 | 8/1974 | Drozdowski et al. | 364/416 X |
| 3,861,877 | 1/1975 | Matharani et al. | 356/39 X |
| 4,040,742 | 8/1977 | Ito et al. | 356/40 X |
| 4,061,469 | 12/1977 | DuBose | 364/416 X |
| 4,086,631 | 4/1978 | Vick | 364/416 |
| 4,125,828 | 11/1978 | Resnick et al. | 364/416 X |
| 4,169,125 | 9/1979 | Rodriguez et al. | 364/497 X |

Primary Examiner—Edward J. Wise
Attorney, Agent, or Firm—Holman & Stern

[57] ABSTRACT

A phasing system is provided for parallel channel continuous flow systems wherein the individual test channels have different flow times although intersample timing is constant. A phasing sample is introduced and its presence is sensed at the output of each of the parallel test channels. The presence of the phasing sample is detected by means of an analog detector, a digitizer, and a digital computation system. After detection of the phasing sample in a channel the time at which it arrives at the detector is marked. Since intersample timing is constant and the time when the sample is introduced into the parallel channels is known, the time at which subsequent samples should arrive at the detector can be established for each channel. Time zones are opened for each channel and each detector which correspond to the times plus or minus a certain tolerance at which subsequent samples can be expected to arrive. In a preferred embodiment, two light emitting diode/phototransistor combinations operating on different frequencies are utilized to give a differentiated output upon sensing the presence of a colored phasing solution at the beginning of a automated blood grouping process.

12 Claims, 5 Drawing Figures

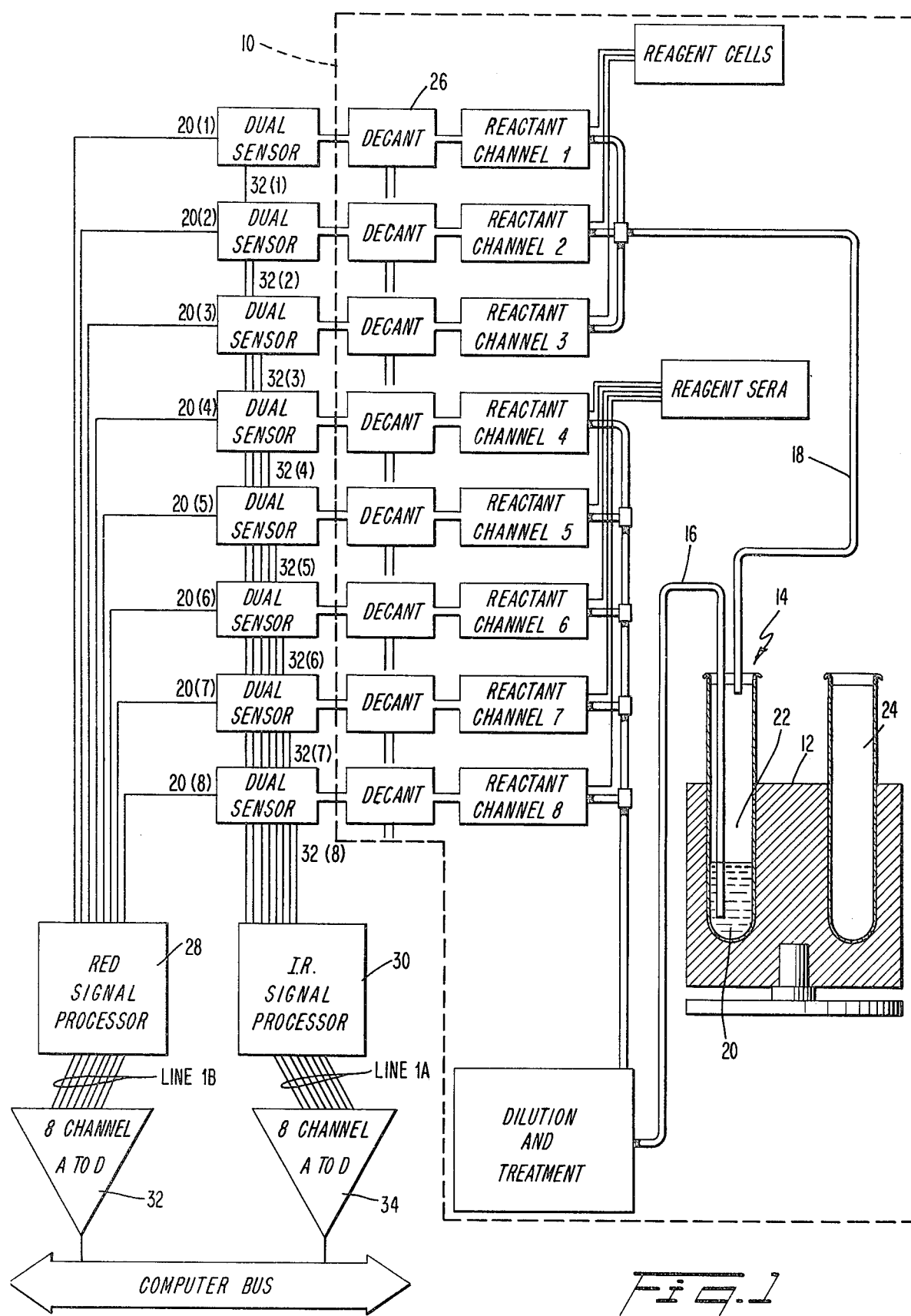

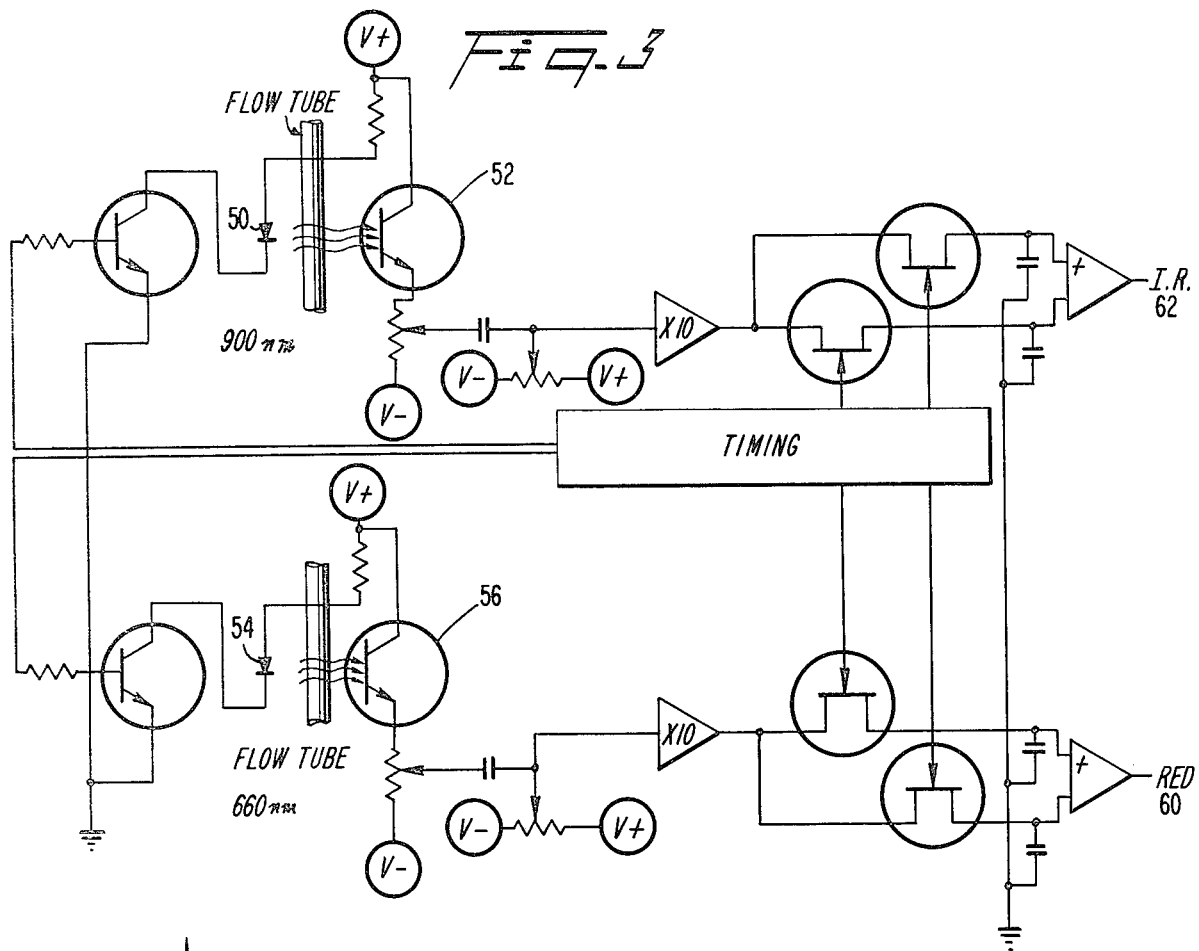
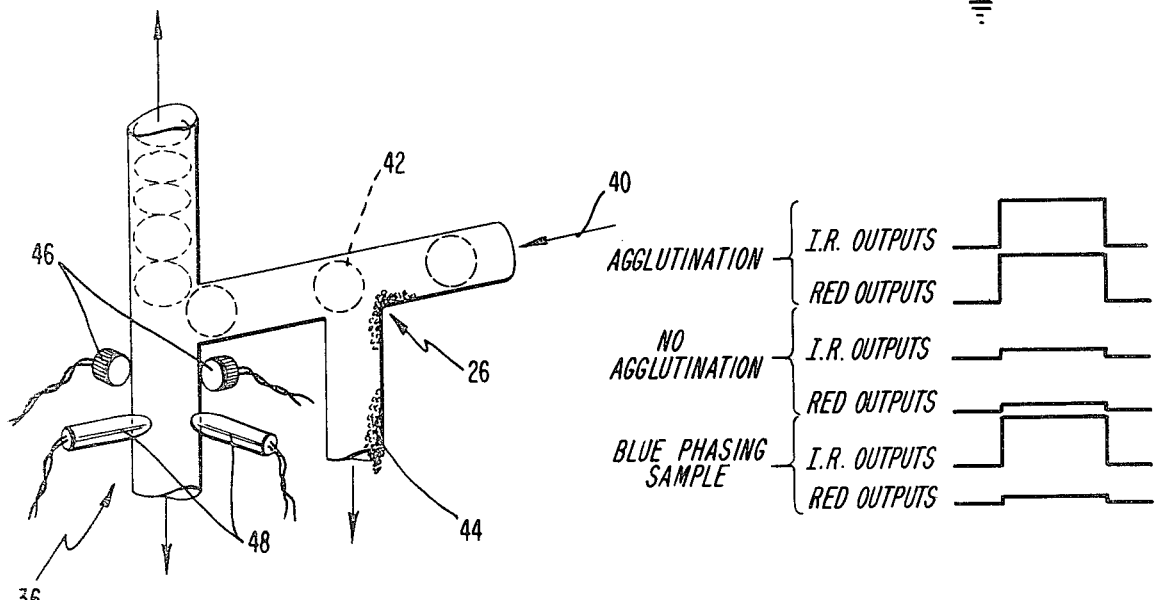

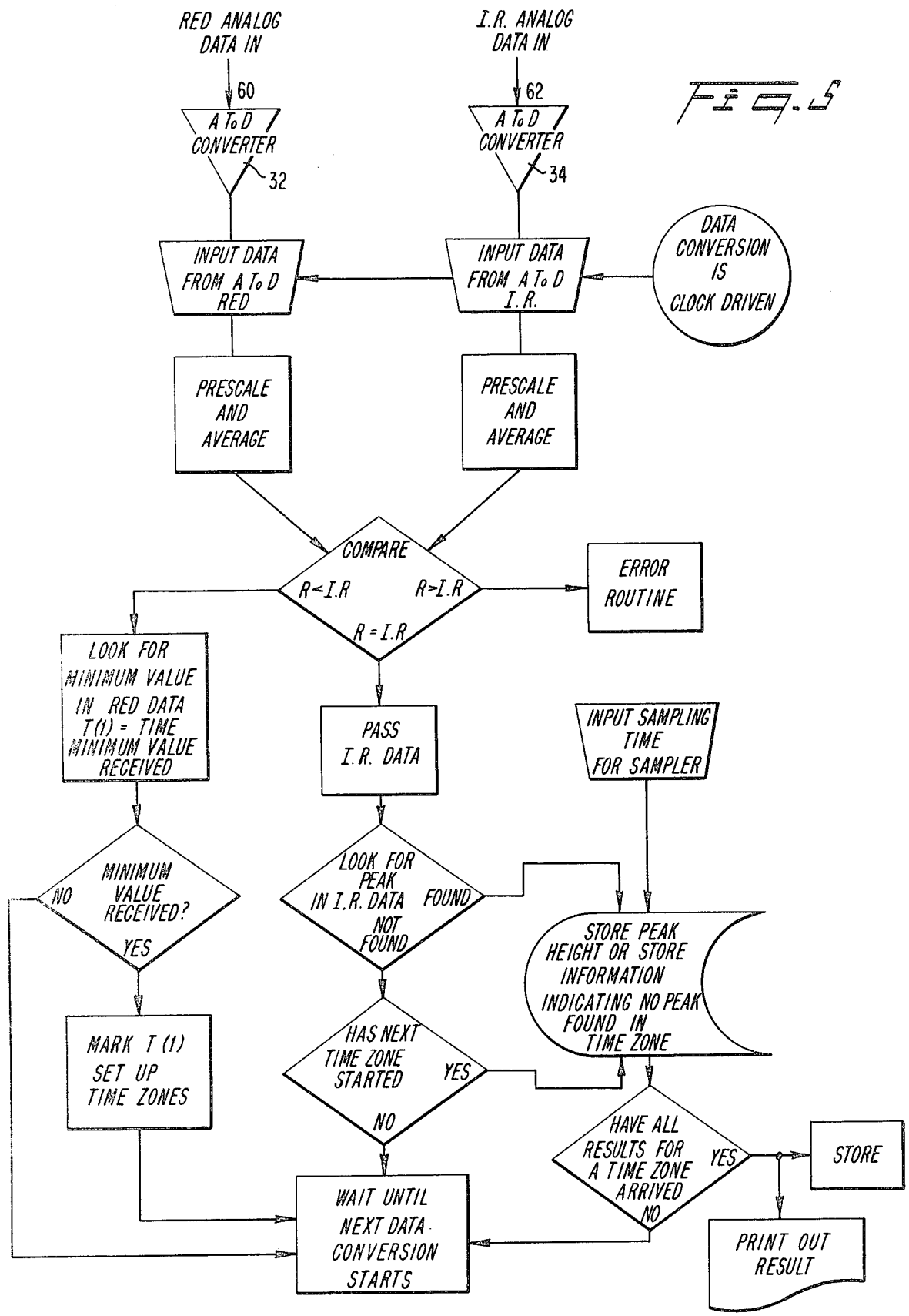

PHASING DETECTOR FOR CONTINUOUS FLOW SYSTEMS

BACKGROUND OF THE INVENTION

The present invention generally relates to phasing systems for continuous flow test systems and more specifically to an apparatus to enable completely automated blood sample testing.

In continuous flow systems in general and in blood-grouping machinery in particular, many individual samples are sequentially pumped through the same dividing, mixing, reaction and settling coils. The basic approach is to utilize the same tubing for processing many samples. The liquid reactants are propelled through the tubing in the systems by a metering pump system utilizing air bubbles to maintain separation between differing liquids. Typically, a sample which is segmented by several air bubbles will also be separated from the next sample by a wash solution. One example of such a continuous flow system is the Blood Grouping AutoAnalyzer manufactured by Technicon Corporation.

The Blood Grouping AutoAnalyzer makes use of the well known antibody-antigen reaction used in manual blood grouping. In "forward" grouping, well characterized antibodies contained in the sera of a known blood group are used as the reagent. These are reacted with unknown red cells contained in the sample. These red cells are obtained using a double sampling probe on a centrifuged whole blood sample. The upper probe samples the unknown plasma with the lower probe sampling unknown red cells. In "reverse" grouping, well characterized red cells ae used as the reagent. Unknown plasma from the upper probe is reacted with the reagent cells.

Regardless of whether forward or reverse grouping is performed, the mixing of red cells and plasma or serum is involved. The antibodies contained in the plasma or serum can attach to more than one red cell, and when they do, bridges are formed. When multiple bridges are formed, visible clumping of red cells or "agglutination" is noted. A reaction is termed positive if agglutination occurs. In the Blood Grouping AutoAnalyzer, a single sample is reacted with both known typing sera and known reagent cells in a parallel fashion. From the pattern of positive and negative reactions, the blood group and Rh factor can be established.

The currently available AutoAnalyzer equipment allows reactions to proceed to conclusion in a reaction manifold. At the end of each reaction coil contained in the manifold, a decant port in the bottom of the exit tube collects sedimented agglutinates. The output of the parallel reactant channels are then deposited on a moving belt of filter paper for subsequent manual interpretation. Unfortunately due to irregularities in glassware and pump tubing, the transit time for various reactant channels will differ. Clearly it would be ideal to have the output of each parallel reactant channel for a given blood sample simultaneously placed on a filter paper belt to facilitate comparison of the reaction products. The length of tubing connecting the output of a reactant channel with the moving belt of filter paper is generally varied such that all samples are in fact simultaneously applied to the moving filter paper.

Unfortunately, after several hundred samples, it is not uncommon for one or more channels to lead or lag the other channels very slightly such that towards the end of a three hundred sample batch, it would be unascertainable as to whether an agglutination reaction is attributable to sample 296 or 297 leading to inaccuracies and errors which are intolerable as far as the matching and categorization of human blood is concerned. These errors are generally overcome by virtue of the fact that a trained operator is necessary to visually categorize the reactions and tabulate the results and can factor out any lead or lag in the individual channel transit times.

In the past, various fully automated read out systems have been proposed with varying degrees of success. One such modification of the Blood Grouping AutoAnalyzer is described in "Automated Read Out of the BG-8 Blood-Grouping Machine" published in *Vox Sanguinis*, Vol. 30:445-452 (1976) subject matter thereof herein incorporated by reference. There a light emitting diode and a photo-diode sense the existence of a positive or negative reaction by virtue of the clarity or turbidity of the fluid passing through a clear tube located between the diodes located in the reaction stream after decantation of the agglutinates has occurred. In this scheme, the existence of a clear region in a reaction tubing is indicative of a positive reaction since the results of a positive reaction (agglutination) are removed (by decantation) before optical detection. In a subsequent publication "Automated Read-Out of Sample Identification and Test Results in a BG-8 Blood Grouping Machine," *Vox Sanguinis*, Vol. 33:108-115 (1977), a certain degree of success was reported although it was noted that synchronization was effected by varying the length of transmission tubing between the reaction channels and the optical sensor unit. However, this device would still require manual monitoring because due to the occurrence of protein deposits occurring in one or more of the channels, the synchronization of the system must be corrected each time a new tray of samples is installed for sampling. This necessity for resynchronizing the output of the sampler severely limits the "automated" aspect of the machinery and still requires a skilled technician for large volume operations.

SUMMARY OF THE INVENTION

In view of the foregoing, it is an object of the present invention to provide a completely automatic means for synchronizing or phasing the output of reactant channels in a continuous flow test system.

It is a further object of the present invention to provide an apparatus for automatic data acquisition and synchronization of acquired data to provide usable information on the desired characteristic of test samples.

It is a still further object of the present invention to provide an apparatus for determining and recording blood grouping data utilizing existing automatic analyzing systems.

It is an additional object of the present invention to provide a method whereby blood grouping information in a plurality of channels can be correlated to individual samples.

In accordance with the above and other objects, one preferred embodiment of the present invention places a phasing sample in the first of 40 blood samples to be tested. The phasing sample traverses the reaction tubes and is sensed at the output of the reaction channels. Analogue data from a pair of light emitting diode/photo-transistor combinations mounted on the reaction coils is digitized and put directly into a computer bus. Processing software is adapted to detect the existence of a phasing sample passing through the reaction detector of each channel. Because intersample timing is regular for all channels, time zones are established for an individual channel such that the arrival of the next sample can be specified after a phasing sample is passed through all channels. Time zones are centered sequentially on $T(1)+(n-1)t$ where $T(1)$ is the time the phasing sample is detected, t is the intersample spacing and n is the tray position number. Clearly for all channels, data occurring within the same time zone can be meaningfully correlated as having been derived from a single sample.

BRIEF DESCRIPTION OF THE DRAWINGS

A more complete appreciation of the invention and many of the attendent advantages thereof will be readily apparent as the same becomes better understood by reference to the accompanying drawings wherein:

FIG. 1 is a block diagram schematically indicating the operation of an eight-channel Blood AutoAnalyzer in accordance with the present invention;

FIG. 2 is a perspective view showing the decant and dual sensor apparatus;

FIG. 3 is an electrical schematic showing the red and infrared signal processors;

FIG. 4 is a waveform comparison of red and I R outputs; and

FIG. 5 is a computer flow diagram indicating one logic pattern applicable to the present invention.

DETAILED DESCRIPTION OF A PREFERRED EMBODIMENT

Referring now more particularly to the drawings wherein like numerals designate like parts throughout the several views and more particularly to FIG. 1 wherein the dotted line portion 10 indicates a conventional AutoAnalyzer. A rotating carousel 12 sequentially places blood sample tubes 14 in appropriate position to be sampled by cell probe 16 and plasma probe 18. These probes are sequentially extended into centrifuged blood samples such that the cell probe 16 extends into the area of red cells 20 with the plasma probe 18 extending only into the area of plasma 22. Additionally shown is a sample tube filled with a phasing sample 24 which in a preferred embodiment contains a blue dye sample.

In a preferred embodiment, the plasma probe 18 supplies plasma to reactant channels 1-3 which are also supplied with reagent cells. Similarly cell probe 16 supplies red cells after appropriate dilution and treatment to reaction channels 4-8 which are also supplied with reagent sera. The reactant channels allow the appropriate mixing between the reagent and blood sample materials and depending upon whether there is "forward" or "reverse" grouping, the pattern of agglutination or the lack of it will be an indication of the blood samples group and/or Rh factor. In a conventional AutoAnalyzer, the agglutinates are decanted or separated from the fluid flow with the fluids output supplied to a moving strip of filter paper (not shown) from which the grouping information is determined.

In the present invention however, the fluid output of the decant devices 26 is supplied to an optical sensor which has two outputs, a red output and an infrared output (in a preferred embodiment). The red and infrared (I R) outputs of each sensor means are supplied to red and I R signal processors 28 and 30 after conditioning of the red and I R signals, they are applied to red and I R analog-to-digital converters 32 and 34, respectively, which supply outputs to the computer bus. Although separate red and infrared signal processing and analog-to-digital converters have been shown (for clarity of understanding) it is clear that with a suitable multiplexing system, a single signal processing and analog-to-digital converter could be utilized and such is the case in a preferred embodiment of the invention.

A better understanding of the decant device 26 and the dual output sensor means 32 can be had by reference to FIG. 2. An input 40 from a reactant channel supplies the decant device 26 with the products of the reactant channel. As previously noted, the samples, wash solutions, etc. when traveling through the reactant channels, are segmented by air bubbles 42. In the event agglutination occurs, the agglutinate 44 is decanted or removed from the major liquid flow. Where agglutination does occur, the remaining liquid is an order of magnitude clearer than the non-agglutinated blood sample and the indication of this relative clearness of the liquid is easily detectable by a conventional light emitting diode/photo-transistor placed on opposite sides of a glass tubing through which the liquid is passed.

In the embodiment shown in FIG. 2 however, the air bubbles 42 are removed by flotation with the liquid being passed in a downward direction past two light emitting diode/photo-transistor combinations. In a preferred embodiment, the light emitting diodes 46 are located opposite photo-transistors 48 such that the light path from one light emitting diode/photo-transistor combination crosses the light path from the other combination. This has the advantage of sensing the same liquids at the same time with both combinations. The electronic circuitry and signal processing functions are clearly set forth in FIG. 3 although it should be understood that many varients to such signal processing circuitry will be obvious to those of ordinary skill in the art. In this embodiment, the infrared light emitting diode 50 transmits light at 900 nm through the flow tube to infrared sensitive phototransistor 52. Similarly, the red light emitting diode 54 transmits red light at 660 nm through the flow tube to the red sensing photo-transistor 56. After appropriate processing, red and infrared output signals 60 and 62 are provided.

FIG. 4 is a schematic indicating the instantaneous outputs of the infrared and red processing circuits for a sampling period during the conditions of agglutination, non-agglutination, and the sensing of a blue phasing sample. The outputs of FIG. 4 illustrate the relationship of red to I R and are not absolute. It will be remembered that after agglutination, the liquid passing through the flow tube is relatively clear and thus a relatively high output would be present from both the infrared and red channels of the sensor. However, without agglutination, the presence of cell matter between the light emitting diodes and photo-transistors would cause a relatively diminished output in both sensors. If a blue phasing sample is present, the blue color will tend to obstruct the red light more than the infrared light resulting in a decrease in red output without a corresponding decrease in I R output. The blue dye used in the preferred embodiment is commonly referred to as Brilliant Blue FCF. Thus, in a preferred embodiment if a blue phasing sample is utilized, any great disparity between the red and I R outputs will be indicative of the presence of a blue phasing sample. It will be obvious to those of ordinary skill in the art that if different colored phasing samples are desirable, different wavelength light emitting diode/photo-transistor combinations will provide the same positive indication of the presence of a phasing sample. The advantage of utilizing two sensors is that regardless of the transmissivity of the sample between the light emitting diode and the photo-transistor, the change in the ratio of I R to red output will be relatively constant upon encountering the blue phasing sample. Thus the indication of the presence of a phasing sample will be independent of the transmissivity of the fluid. This factor may be of particular importance in numerous continuous flow systems wherein the transmissivity varies over a large scale and a conventional single diode/photo-transistor pair would not be able to distinguish the presence of a phasing sample.

The data processing means can be any programmable digital computer which can utilize any one of a number of algorithms for phasing and ultimately blood group determination. Two key concepts are utilized in any algorithm for processing of the information: time zones and peak detection. In the preferred embodiments, applied to blood grouping with a conventional AutoAnalyzer when modified as noted above, the intersample time (the time between sampling of one sample tube and its adjacent sample tube) is usually thirty seconds and thirty seconds will be used throughout the rest of the discussion although it should be understood that the intersample time could be greater or less than thirty seconds.

One flow diagram of the decision making process involved in setting up the time zones is outlined in FIG. 5. It should be understood that the setting up of time zones can be done independently for each channel and although FIG. 5 is primary concerned with the setting up of time zones for a single channel, it is nevertheless representative of the process utilized in all channels. The definition of time zone is that period of time in which a sample can be expected. If the intersample spacing is thirty seconds, a time zone will be thirty seconds in duration. For instance after a peak output is detected which indicates a phasing sample has been detected, the time zone for receipt of the first blood grouping sample will start fifteen seconds after the peak and end forty-five seconds after the peak. Subsequent time zones occur in sequential order starting at $15+(n-2)$ 30 seconds and ending at $15+(n-1)$ 30 seconds.

During the initial set up procedure, (called the initialization) a clear fluid is passed through the flow tubes in order to establish base line outputs for the red and I R sensors. This step is called pre-scaling and can extend over a substantial period of time in order to ensure that any contaminants have been washed away and that the clear sample has reached all sensors. An initial phasing solution can be applied and in the preferred embodiment would be a blue dye sample. Then the scaling standard is supplied to all channels which serve to establish the levels of outputs which are indicative of either an agglutination or nonagglutination reaction. After the scaling standard has been applied, the system is ready for operation. It should be pointed out that the calibration which is effected in the prescaling step serves to account for electrical and reagent differences among the channels. It can easily be understood that the light emitting diodes and photo-transistors utilized can be significantly different in sensitivity. One output may be on the order of 3 volts while the other solution may have an output of 5 volts, both with sensor viewing the clear prescaling liquid.

After prescaling, the red and I R outputs are compared. If, in this preferred embodiment, the red output is 20% or more below the I R output, the computer interprets this as the onset of a phasing sample.

After prescaling and utilizing the scaling standard, the system is ready for the first blood grouping samples. Generally these samples will be stored in the carousel tray having a large number of storage spaces which are sequentially sampled with a constant intersample spacing. In each tray at least the first sample would be a phasing sample with additional phasing samples inserted if the throughput time in the various reaction channels are varied widely. After start up, the time at which each new tube is sampled is marked. Analog data is periodically input from the analog-to-digital converters 32 and 34, respectively. In a preferred embodiment, data is sampled eight times per second and averaged over this one second period such that one data point represents one seconds worth of data. This data is scaled relative to the standards previously passed through the optical detectors during the initialization of the system.

In the preferred embodiment, the algorithm acts on not only the newest seconds worth of data, but the last three seconds worth as well and trends prior to the above-mentioned four seconds worth of data are stored. During peak detection, for a data point to be declared a peak, it must pass several criteria. In the case of peak detection for phasing sample, a negative peak is desired since the blue dye absorbs red light causing a drop in red output. Initially then, the trend indicator should show a monotonically decreasing output trend prior to the occurrence of the minimum value. Secondly, it should be noted that of the four stored data points one is a minimum and the transmission levels for the points occurring before and after the minimum are greater. Thirdly, values occurring after the minimum continue to monotonically increase in value.

Meeting the above criteria, a point that has been determined to be a minimum value and the time at which it occurred is then retained in the memory. This time is also passed on to a routine which sets up time zones as previously noted. To ensure against passing a relative minima to the time zone routine which may not be an absolute minima, the minimum will be compared against new values for the next ten seconds. If no lower values are found, the minimum is declared to be an absolute minimum. After an absolute minimum is determined, there will be a full five seconds before time zone 2 is started so that no confidence in the absolute minimum need be sacrificed.

The foregoing is a description of how time zones are set up for a single channel although in the preferred embodiment this process is performed simultaneously for all channels. During normal operation, only the I R data is utilized for determining agglutination/non-agglutination in the reactant channels. However, the red data is continuously monitored and compared with the I R data and when the red data falls 20% or more below the I R data, the presence of a phasing sample is determined and the time zone initiation sequence is started or restarted.

In "forward" grouping, the reagent is a clear typing sera and in FIG. 1 this is applied to reactant channels 4–8 and mixed with the centrifuged red cells 20. If a positive reaction occurs the resultant agglutination will yield a high transmission "clear" indication. Thus a negative indication will be a low output in either of the data channels and this low output will be in the form of a negative peak. If no negative peak is detected in a given time zone, it is assumed that the results was positive.

In "reverse" grouping the background or reagent transmission level is low due to the opacity of red cells which are used as a reagent and applied, as seen in FIG. 1, to reactant channels 1–3. With a positive reaction, the resultant agglutination provides the relatively clear fluid to the sensor which causes a high transmission indication. In "reverse" grouping, the positive peak is sought as an indication of a positive reaction and if no peak is detected in a given time zone the result is assumed to be negative.

The advantages of the dual frequency phasing sample detector can be clearly seen, when it is understood that the addition of reagent cells to reactant channels 1–3 reduces the background transmission to 20 to 35 percent of the transmissivity of reactant channels 4–8 to which reagent sera has been added. The addition of a phasing sample will depress the red channel output to between 2 to 5 percent while leaving the I R channel in its uneffected transmissivity of between 20 and 25 percent. Thus a single channel optical sensor would be unable to distinguish between the presence of a phasing sample or the mere addition of reagent cells to sampled plasma. However, the present invention clearly indicates the presence of the phasing sample regardless of the presence of reagent cells or not.

As a phasing sample can be inserted between any grouping of samples, minor variations in the transit time of the sample through the reactant channel can be compensated for with the result that the time zones always permit different reactions of a single sample to be tabulated together and either printed out or stored as desired.

While the above exemplary description regards the present invention applied to an eight-channel AutoAnalyzer, the invention can be applied to any continuous flow system with any number of channels provided that the analog-to-digital operation (in the case of a multiplex system) is fast enough to scan the total number of channels. Additionally, the data processor must be fast enough to implement the flow chart of FIG. 5 or any suitable alternative for all channels independently in the time between data samplings. Finally, the data buffer or temporary storage must be adequate to store numerous time zones worth of results simultaneously.

Obviously, in view of the above teachings, the internal processing and/or data acquisition can differ without deviating from the scope of the present invention. Rather than utilizing a dual wavelength detector and a colored dye, a single detector and another parameter such as conductivity, viscosity, etc., of the phasing sample could be utilized. As such, it is not necessary to utilize light transmissive detectors at all. And other means of detecting the agglutination reaction could be utilized. Even within the above enumerated preferred embodiment, different colors, LED/phototransistor combinations, algorithms, etc. could be utilized without departing from the spirit of the applicants' invention. Thus it will be seen by those of ordinary skill in the art, that in view of the above disclosure, the present invention can be practiced other than as specifically disclosed herein and the invention is only limited by the scope of the claims appended hereto.

The embodiments of the invention in which an exclusive property or privilege is claimed are defined as follows:

1. In a continuous flow test system, having a plurality of sensor channels, each channel including means for providing an output related to a characteristic to be measured in said channel, an apparatus for phasing data output from those channels when the time delay of sample flow through a channel varies, said apparatus comprising:
   a phasing sample, introducable into said sample flow in said channels, having a detectable characteristic;
   means for detecting and providing an indication of the presence of the phasing sample in each of said channels; and
   data processing means, responsive to said indication, for measuring and reporting the time delay of said phasing sample through each channel and correlating the time delays of each channel with output from said means for providing, said data processing means providing said characteristics to be measured in each channel at a predetermined time regardless of variations in time delays among channels.

2. The apparatus of claim 1 wherein each sensor channel is a reactant channel in which the sample flowing therethrough is being tested to determine the sample reaction to known quantities and said means for detecting includes said means for providing which comprises sensor means for determining the reaction in each of said reactant channels.

3. The apparatus of claim 2 wherein said sensor means comprises a light emitting diode/phototransistor combination for providing an electrical indication of the reaction in said reactant channel.

4. The apparatus of claim 2 wherein said sensor means includes means for distinguishing between a phasing sample and said reaction in said reactant channels.

5. The apparatus of claim 4 wherein said sensor means comprises a light emitting diode/photo-transistor combination for providing an electrical indication of the reaction in said reactant channel.

6. The apparatus of claim 4 wherein said means for detecting includes two light emitting diode/photo-transistor combinations, each of said combinations operating on a different wavelength and said phasing solution detectable characteristic being color, with the reaction determination being the relative level of light transmittance through a channel and said phasing sample determination being a predetermined disparity between the outputs of said transistors.

7. The apparatus of claim 1 wherein each sensor channel is a reactant channel in which the sample flowing therethrough is being tested to determine the sample reaction to known quantities and said means for detecting comprises two light emitting diode/photo-transistor combinations, each of said combinations operating on a different wavelength and said phasing sample detectable characteristic being color.

8. The apparatus of claim 1 including a clock pulse means for periodically sequencing said data processing means such that data outputs from said sensor channels are provided to an output device.

9. A method of blood grouping utilizing an apparatus with a plurality of sensor channels, each channel with a means for measuring a blood grouping characteristic and a means for detecting the presence of a phasing solution, said apparatus capable of automatically sampling a plurality of blood samples, said method comprising the steps of:

applying a phasing sample to said apparatus for sampling;

recording the time delay, between the initial sampling of the phasing sample and the detection of the presence of the phasing sample by said means for detecting, for each channel; and recording data from said means for measuring in accordance with said recorded time delay such that the data from the channels corresponds timewise to a single blood sample regardless of variations in different channel time delays.

10. The method of claim 9 wherein prior to said applying step, said method includes the scaling step of supplying a known standard sample to said apparatus in order to establish the proper operating response of the means for measuring in each channel.

11. The method of claim 10 wherein prior to said supplying step, said method includes a first timing step where a phasing sample is supplied to said apparatus for establishing the time delays necessary for correlation of data in said supplying step.

12. The method of claim 11 wherein prior to said first timing step, said method includes a prescaling step wherein a clear solution is applied to all channels for the initial zeroing of each said means for measuring.

* * * * *